United States Patent [19]

Zakowski et al.

[11] Patent Number: 4,908,320
[45] Date of Patent: Mar. 13, 1990

[54] ANALYZER OPERATING METHOD

[75] Inventors: Jack J. Zakowski, Anaheim; Vincent A. Cuomo, San Bernardino; Gordon C. Blanke, Brea; Richard C. Meyer, La Habra, all of Calif.

[73] Assignee: Beckman Instruments, Inc., Fullerton, Calif.

[21] Appl. No.: 355,061

[22] Filed: May 18, 1989

Related U.S. Application Data

[63] Continuation of Ser. No. 884,461, Jul. 11, 1986, abandoned.

[51] Int. Cl.⁴ .............................................. G01N 35/06
[52] U.S. Cl. ....................................... 436/45; 422/64; 422/67
[58] Field of Search ..................... 436/45, 44, 63–67, 436/72, 73

[56] References Cited

U.S.\PATENT DOCUMENTS

| | | | |
|---|---|---|---|
| 3,081,158 | 3/1963 | Winter | 422/64 |
| 3,225,628 | 12/1965 | Anthon . | |
| 3,542,515 | 11/1970 | Scott | 422/64 |
| 3,814,582 | 6/1974 | Rohrbagh et al. | 23/230 |
| 3,909,203 | 9/1975 | Young et al. | 23/253 |
| 4,166,483 | 9/1979 | Nordlund | 141/1 |
| 4,276,051 | 6/1981 | Ginsberg et al. . | |
| 4,315,735 | 2/1982 | Yamashita et al. | 422/67 |
| 4,457,893 | 7/1984 | Takekawa | 422/64 |
| 4,459,265 | 7/1984 | Berglund | 422/64 |
| 4,629,703 | 12/1986 | Uffenheimer | 436/45 |

FOREIGN PATENT DOCUMENTS 0078948 5/1983 European Pat. Off. .

Primary Examiner—Michael S. Marcus
Attorney, Agent, or Firm—William H. May; Arnold Grant; Gary T. Hampson

[57] ABSTRACT

A method of operating a clinical analyzer wherein the analyzer includes a plurality of reaction locations divided into two groups. Predetermined operations are performed on the first and second groups during corresponding processing cycles. A process that is common to both cycles is performed simultaneously for reaction locations in the first and second groups during only one of the cycles. The other of the cycles can thus accommodate operations unique to particular tests that would not otherwise be available on the analyzer. The common process may be washing of adjacent reaction locations included in the first and second groups.

20 Claims, 3 Drawing Sheets

FIG. 1

ANALYZER OPERATING METHOD

This is a continuation of co-pending application Ser. No. 884,461, filed on July 11, 1986, now abandoned.

BACKGROUND

The present invention relates generally to the field of analytical instruments and more particularly to operating methods and techniques for such instruments.

Clinical analyzers are well known in the art for analyzing patient samples to determine the presence and/or concentrations of substances in such samples. The analyzers may be very simple, single analyte instruments that require many of the steps in an analysis to be performed by an operator. For example, the operator may be required to place the individual sample onto the analyzer, add reagents to the sample, time the reaction, and read a resulting value from the analyzer. The value would then be compared to calibration values by the operator to determine a final result, often in terms of analyte concentration in the patient sample.

The more sophisticated clinical analyzers generally perform many or most of these and other steps automatically. If an automated analyzer is dedicated to performing a limited number or menu of analyses for each sample, then the operator need only place patient samples onto the analyzer and start the analyzer operation. Other automated analyzers offer a menu of tests that may be performed for each sample, requiring that the operator specify the particular tests required.

Each automated analyzer can be considered as having a characteristic operating method. For example, some analyzers perform all tests requested for a sample before beginning the analysis of a next sample. Other analyzers treat each test requested for a sample individually, performing each such test as a separate subcycle of the overall operation of the analyzer. In such analyzers, there may be a number of tests in progress at any one time. Different tests may be simultaneously under way for one sample while the same tests may be in progress for several different samples. Analyzers of this latter type are often referred to as "random access" analyzers.

Every test or chemistry on an analyzer has its own particular requirements, including the reagents needed and the processing time for the test. Some tests use only one reagent, while other tests may require several reagents or the addition of a trigger reagent to begin a timed reaction sequence. The processing time may not be critical for some tests, with others requiring specified incubation and reaction times that must be precisely observed.

As the number of tests on the menu of a random access analyzer increases, the number of different requirements for such tests also increases. This added complexity affects the analyzer throughput, that is, the number of samples that the analyzer can process in a given time.

Thus there is a need for a random access clinical chemistry analyzer that can maximize throughput while retaining a large menu of available chemistries. There is also a need to provide an operating method for such an analyzer that provides sufficient variability and adaptability so that new chemistries can be added to the menu without requiring modification of the operating method or the analyzer itself.

SUMMARY OF THE INVENTION

The present invention is directed to a method of operating a random access analyzer that meets the objectives set forth above. An operating method in accordance with the present invention is adapted for use on an analyzer that includes a plurality of reaction locations for conducting analyses of samples. The locations are divided into a first group and a second group. Predetermined operations are performed on the first and second groups during corresponding first and second processing cycles. Advantageously, a process that is common to reaction locations in both the first and second groups is performed during only one of the first or second cycles. In doing so, the other of the first or second cycles can accommodate operations unique to particular tests that could not otherwise be available on the analyzer.

In the embodiment disclosed herein, the common process is the washing of adjacent reaction locations. During the cycle where washing is not performed, the operations may include injecting reagents into reaction locations that would not otherwise be accessable if washing were required during both the first and second cycles.

The method may further include dividing the reaction locations into active and inactive locations. Active locations are those where reagents and sample are injected. All reaction locations in the first group may be active while selected ones of the reactions locations in the second group are active. An inactive reaction location in the second group enables reagent injection into an active location in the first group to thus accommodate multicomponent reagents and trigger reagents.

Brief Description of the Drawings

FIG. 1 is a simplified diagram of the working surface of a random access analyzer which may utilize the operating method of the present invention.

DETAILED DESCRIPTION

Figure 1:
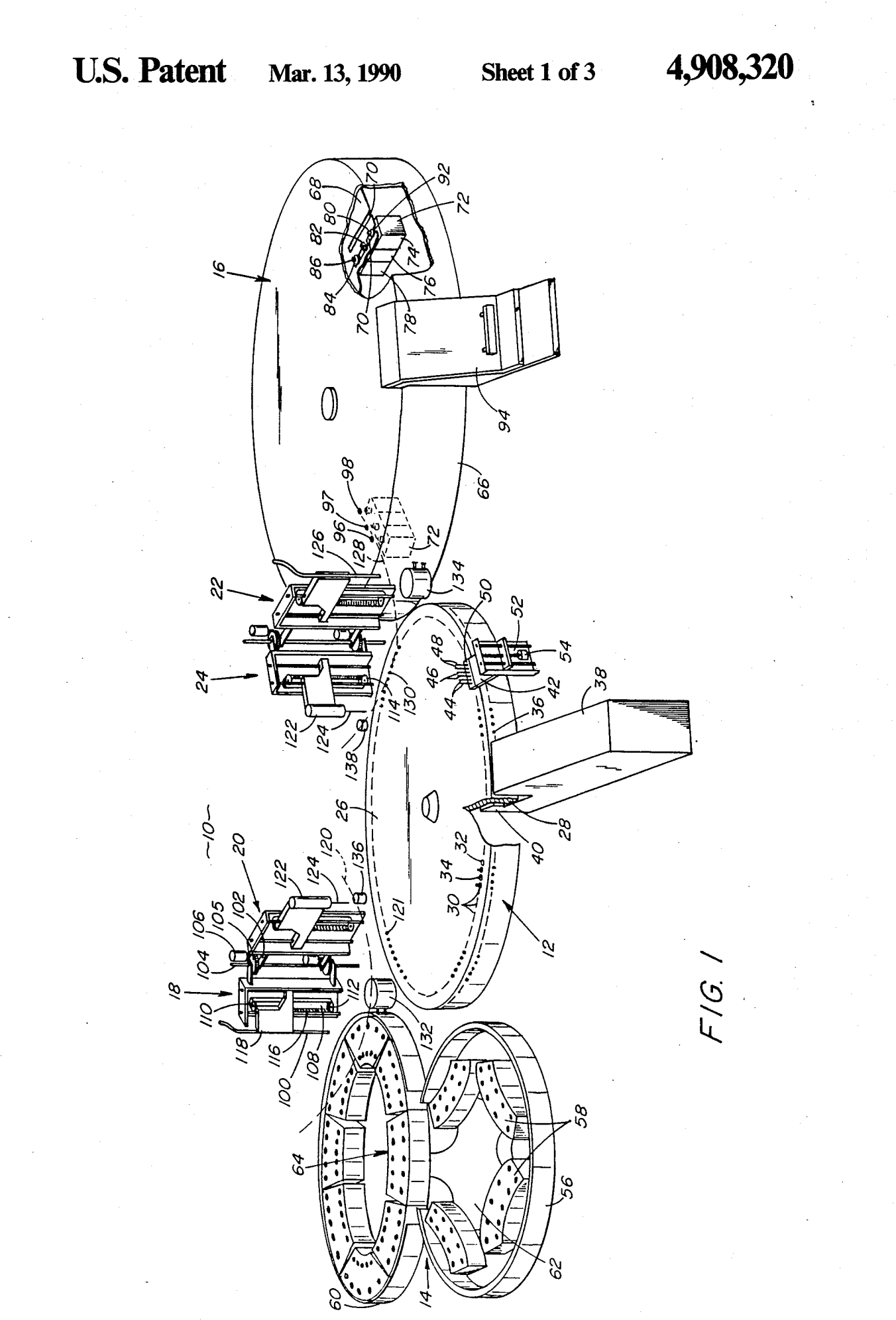
Figure 2:
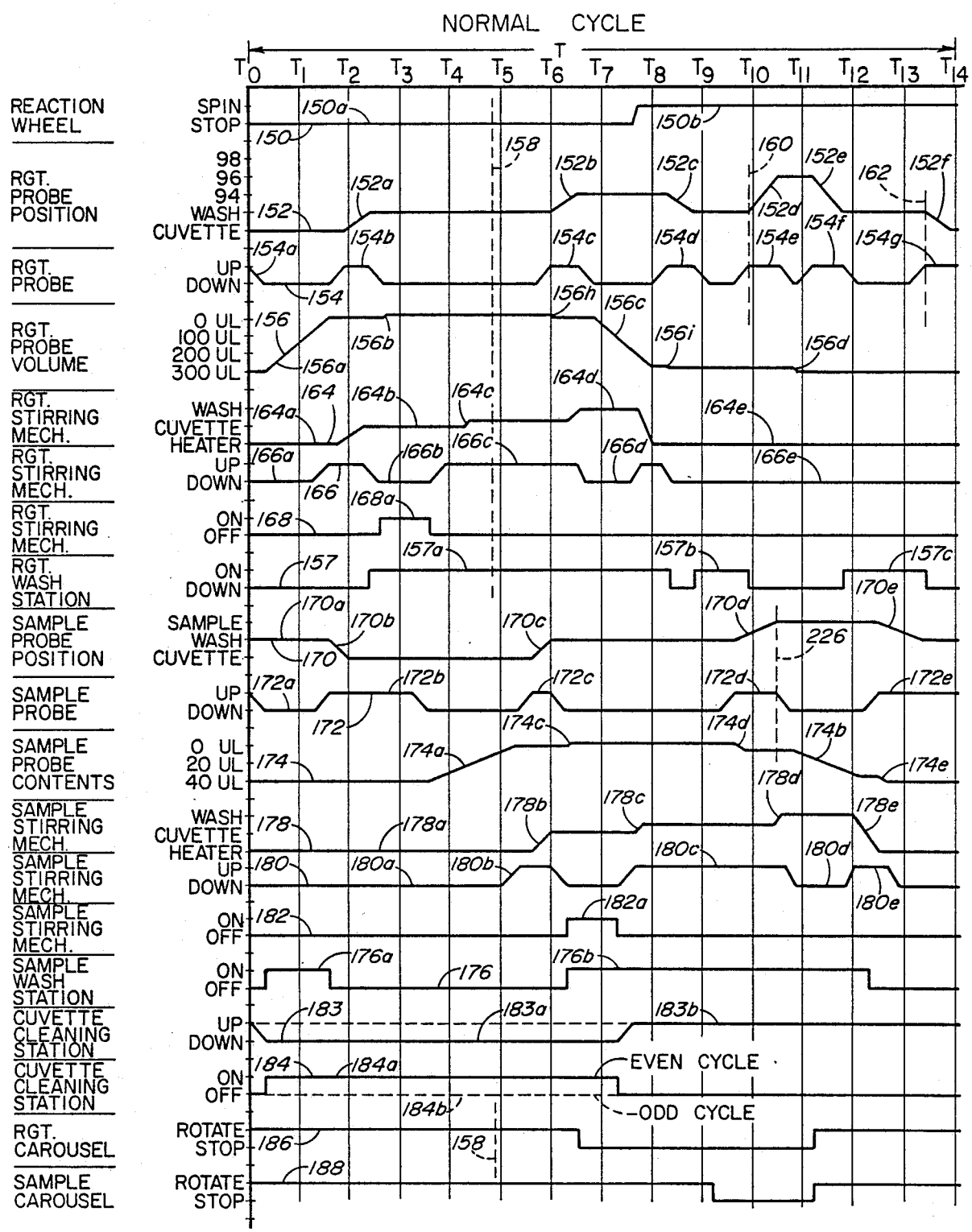
FIG. 2 is a timing diagram of actions occurring on the working surface of FIG. 1 during a first cycle timing of the operating method of the present invention.

With reference to FIG. 1, an automated clinical analyzer suitable for use with the method of the present invention includes a horizontal working surface 10 which supports a reaction wheel 12, a sample loading and unloading apparatus 14, a reagent storage carousel 16, sample transfer and stirring mechanisms 18 and 20, respectively, and reagent transfer and stirring mechanisms 22 and 24, respectively. The reaction wheel 12 comprises a generally flat hub or central portion 26 and a depending ring-like portion 28 at the periphery of the wheel 12. A plurality of reaction locations 30 are defined in the periphery of reaction wheel 12, each of the reaction locations 30 comprising a vertical hole 32 into which may be placed a reaction cuvette 34. In the embodiment disclosed herein, there are eighty such reaction locations 30. Openings 36 are formed through the ring-like portion 28 to define an optical path through each of the reaction locations 30 and associated cuvettes 34.

A polychromatic analysis device 38 is positioned at the periphery of the reaction wheel 12. A portion 40 of the device 38 extends under the reaction wheel 12 and behind the ring-like portion 28. The portion 40 of the device 38 includes a light source and optics for directing a beam of light through the openings 36. The beam of light passes through the openings 36 and is detected and processed to yield analyte concentrations as is known in the art. In the embodiment disclosed herein, the analysis device 38 is a flash photometer and includes a flash tube that is triggered when the optics in the device 38 are aligned with each of the openings 36. As the reaction wheel 12 rotates at, for example, ninety r.p.m., the flash photometer operates to produce a plurality of polychromatic photometric readings for each of the reaction locations 30.

A cuvette cleaning station 42 is also located at the periphery of the reaction wheel 12. The station 42 has two wash probes 44, two rinse probes 46, and two drying probes 48 positioned above the reaction locations 30 and connected to suitable vacuum and fluid sources (not shown). The wash and rinse probes 44 and 46 each comprise concentrically disposed fluid delivery and vacuum conduits such that wash and rinse fluids may be simultaneously delivered into and aspirated from the cuvettes 34. The drying probes 48 simply comprise a single conduit for aspirating any remaining rinse fluid from the cuvettes 34. The probes 44-48 are carried by an arm 50 such that the lower tips of the probes 44-48 lie in a plane perpendicular to the vertical central axis of the reaction wheel 12. The arm 50 is in turn supported by an elevator 52 that is operated by a stepper motor 54 for raising and lowering the arm 50 and the probes 44-48. With the arm 50 in its raised position, the tips of the probes 44-48 are above the tops of the cuvettes 34. When the reaction wheel 12 is stopped and the arm 50 is in its lowered position, the tips of the probes 44-48 are disposed within a group of six adjacent cuvettes 34. In particular, the probes 44-48 are spaced such that sets of two adjacent cuvettes 34 may be simultaneously washed, rinsed, and dried when the probes 44-48 are lowered by the arm 50 into the cuvettes 34.

The sample loading and unloading apparatus 14 includes a loading tray 56 which receives and supports four arcuate sample sectors 58. Each of the sample sectors 58 includes ten wells to receive individual sample cups. The cups hold, for example, patient samples, calibration standards, and the like, all as is well known in the art. The apparatus 14 also includes a sample carousel 60 adapted to hold eight of the sample sectors 58 about the periphery of the sample carousel 60. The sample sectors 58 are transferred between the loading tray 56 and the sample carousel 60 by a transfer mechanism 62. The transfer mechanism 62 lifts all of the sectors 58 disposed on the loading tray 56 and the sector 58 disposed at a transfer position 64 on the sample carousel 60 above the sectors 58 disposed on the sample carousel 60. The transfer mechanism rotates clockwise (as viewed from above in FIG. 1) to shift all sectors 58 one position. The transfer mechanism then lowers the sectors 58 back onto the loading tray 56 and the sample carousel 60. The transfer cycle just described thus moves one of the sectors 58 from the tray 56 to the sample carousel 60 at the transfer position 64, transfers the sector 58 at the transfer position 64 to the loading tray 56, and increments the remaining sectors 58 on the loading tray 56 one position clockwise around the loading tray 56. In the embodiment disclosed herein, the transfer mechanism may include a stepper motor for rotation and may utilize a pneumatic cylinder and piston for vertical displacement. Other means for rotation and vertical displacement would be equally suitable.

The sample carousel 60 may be rotated to position sample cups for transfer of sample volumes from the sample carousel 60 to the reaction wheel 12 as is described below. The sample carousel 60 may include a stepper motor or other suitable rotational means for providing controllable rotational movement.

The reagent storage carousel 16 preferably includes a refrigerated enclosure 66. Disposed within the enclosure 66 is a rotor 68 (shown partially cut away in FIG. 1) having a plurality of radial slots 70 about the periphery thereof. Each of the slots 70 is adapted to support a reagent cartridge 72. The reagent cartridges 72 provide three chambers 74, 76, 78 for the storage of three separate reagents, each of the chambers 74, 46, 78 including necks 80, 82, 84 adapted to be received in the slots 70. The necks define openings 86 through which reagents may be removed. The cartridges 72 may be removeably hung from the rotor 68 by means of collars 92 formed on the necks and are loaded onto and removed from the rotor 68 via an access door 94 in a side wall of the enclosure 66. The reagent storage carousel 16 includes suitable means, such as a stepper motor, to rotate the rotor 68 and thus the reagent cartridges 72 disposed thereon. Access openings 96-98 in a top surface of the enclosure 66 are adapted to be aligned with the openings 86 in the reagent cartridges 72 such that reagents can be withdrawn from the cartridge 72 (shown in phantom in FIG. 1) positioned beneath the access openings 96-98.

The sample transfer mechanism 18 includes a probe 100 adapted to transfer sample volumes from the sample carousel 60 to the reaction locations 30. The probe 100 is connected via a tube to a displacement pump (not shown) in a conventional fashion for drawing sample into the probe 100 and later dispensing the sample as described herein. The mechanism 18 includes a frame 102 that is pivotally fixed to a vertical pivot member 104. The frame is fixed to suitable pivot means such as a gear 105 that is engaged by a stepper motor 106 for rotating the frame 102 about the pivot member 104. The frame 102 supports an elevator 108 in the form of upper and lower pulleys 110 and 112, the lower one of which is driven by a stepper motor 114. The pulleys 110 and 112 carry a belt 116. The probe 100 is fixed to a carrier 118 that is moveable vertically with respect to the frame 102. The carrier 118 is in turn fixed to the belt 116. The stepper motor 114 rotates the pulley 112 and the belt 116 carried thereby translates the rotational motion of the stepper motor 114 to vertical linear motion. This motion is coupled through the carrier 118 to the probe 100, displacing the probe 100 vertically. By controlling the stepper motors 106 and 114, the probe 100 may be displaced about an arc shown by a dashed line 120 and displaced vertically. The arc 120 is above inner and outer sample cups carried by the sample carousel 60 and a sample injection location 121, one of the reaction locations 30 on the reaction wheel 12. Thus, the probe 100 may be controlled so as to access samples carried by the sample carousel 60 and deposit portions of such samples into the reaction wheel 12.

The sample stirring mechanism 20, reagent transfer mechanism 22, and reagent stirring mechanism 24 include vertical and horizontal displacement means similar to those just described for the sample transfer mechanism. The stirring mechanisms 20 and 24 include stirring motors 122 and stirring members 124 rotatable by the motors 122. The stirring members 124 may be a simple straight shaft or may include a slight flair at the tip thereof to promote stirring. The sample stirring mechanism is adapted to rotate along the arc 120 and dip into the cuvette disposed at the sample injection location 121.

The reagent transfer mechanism 22 includes a reagent delivery probe 126 adapted to describe an arc illustrated by a dashed line 128 in FIG. 1 above the openings 96–98 and to a reagent injection location 130 above the reaction locations and fixed relative to the reaction wheel 12. Similarly, the reagent stirring mechanism 24 is adapted to place the reagent stirring member 124 into the cuvette at the reagent injection location 130 for stirring of the fluids contained therein. The sample and reagent injection locations 121 and 130 and the cuvette cleaning station are positioned such that, with the reaction wheel 12 stopped with a cuvette at the sample injection location 121, sample and reagent may be delivered to cuvettes positioned at the injection locations 121 and 130 and cuvettes beneath the wash, rinse and dry probes 44–48 may be cleaned as described above.

Probe wash stations 132 and 134 are disposed along the arcs 120 and 128 for washing the probes 100 and 126 and stirring members 124, all in a conventional fashion. Further, heating stations 136 and 138 are disposed along the arcs 120 and 128. The heating stations 136 and 138 can serve as home positions for the stirring members 124 to heat the stirring members 124 prior to stirring fluids positioned at the locations 121 and 130. Such preheating minimizes the impact stirring may have on the temperature of the fluids at the locations 121 and 130.

It is to be recognized that while a particular embodiment of an analyzer suitable for the method of the present invention has been described, other working surface configurations may be equally adaptable to such method. Furthermore, the apparatus includes suitable control systems for controlling the various elements described above in accordance with the teachings of the present method and in accordance with otherwise well-known automated instrument design principles. Such control systems are common and widely used and are not be further described herein.

The method of the present invention will be described with respect to the physical layout of the working surface 10 and with respect to the timing diagrams of FIGS. 2 and 3.

The reaction locations 30 are divided into equal groups. A first such group includes every other reaction location 30 about the periphery of the reaction wheel 12 and may be designated the "even" group and the second group includes all the remaining reaction locations 30 and is designated the "odd" group.

The method in accordance with the present invention generally can be described as including sequential operating cycles. Each cycle consists of a sample and reagent injection portion followed by rotation of the reaction wheel 12. Each cycle ends with the rotation of the reaction wheel 12 stopped. Except as described below for cycles requiring third or trigger reagent injection, the reaction wheel 12 comes to rest with the reaction locations incremented one position counterclockwise (as viewed from above in FIG. 1) with respect to the sample and reagent injection locations 121, 130 and the cleaning station 42. For example, if a sample injection occurs at an even reaction location during a first cycle, sample injection during the next cycle will occur at an adjacent odd reaction location clockwise from the previous sample injection, and so on for subsequent cycles.

A complete analysis within a typical cuvette begins as reagents are injected into the cuvette at the reagent injection location 130. After a number of cycles, the cuvette advances to the sample injection location 121 where sample is then injected into the cuvette. During subsequent cycles the analysis is completed and the result obtained via the polychromatic device 38. Successive cycles eventually move the cuvette to and through the cuvette cleaning station 42 and back to the reagent injection location 130 to begin another analysis. In the embodiment disclosed herein, there are eighty reaction locations 30 about the periphery of the reaction wheel 12. Each of the odd and even groups of such reaction locations 30 thus comprise forty reaction locations. Furthermore, after operating eighty cycles of the analyzer, a cuvette is ready to begin a new analysis.

The cycles during which sample may be injected into cuvettes in the even group positioned at the sample injection location 121 are designated as "even" cycles. Likewise, "odd" cycles are those during which sample may be injected into a cuvette in the odd group. Even and odd cycles are performed alternately, that is, even, odd, even, odd, and so on. During an even cycle, the cuvette located at the reagent injection location 130 may receive one or two reagents from the reagent delivery probe 126. Also, the cuvette positioned at the sample injection location 121 may receive a sample from the sample delivery probe 100. Concurrent with the delivery of reagents and sample to the appropriate cuvettes, the cuvette cleaning station 42 operates to wash, rinse and dry adjacent pairs of cuvettes as described above. Because adjacent ones of the cuvettes are simultaneously cleaned, the cleaning station 42 cleans cuvettes in both the odd and even cuvette groups during the even cycle. To complete the even cycle, the reaction wheel 12 is rotated several revolutions and the polychromatic device 38 operates to obtain polychromatic colorimetric data for the cuvettes carried by the reaction wheel 12.

As the reaction wheel 12 ends its spinning phase during the even cycle just described, the reaction wheel is controlled so as to come to rest in one of two positions. If the next cuvette in sequence (a cuvette contained in the odd group of cuvettes) is to receive a one or two component reagent injection as is usual during the even cycle, then the reaction wheel 12 comes to rest with the next sequential odd cuvette at the reagent injection location 130. The next cuvette in sequence for sample injection is thus also positioned at the sample injection location 121. Reagent and sample injection then proceed as described above.

However, the cuvette cleaning station 42 does not operate during the odd cycle. Thus, if an otherwise out-of-sequence cuvette on the reaction wheel 12 requires a third or trigger reagent component to be injected therein, the reaction wheel 12 instead comes to rest with such cuvette located at the reaction injection location 130. The third or trigger reagent is then injected into such cuvette. Advantageously, because the cuvette cleaning station 42 is not in operation during the odd cycle, the reaction wheel 12 is free to rotate to bring the next cuvette in sequence for sample injection under the sample injection location 121. Sample injection then takes place at the same time in the odd cycle that sample injection would otherwise occur if a one or two component reagent injection had taken place. This enables the timing of data points taken during reaction wheel 12 rotation to be synchronized from cycle to cycle. Subsequent rotation of the reaction wheel 12 takes place as described above with the reaction wheel 12 coming to rest with the next even cuvettes in sequence beneath the sample and reagent injection locations 121 and 130.

The even and odd cycles as just described both accommodate one or two reagent injections, suitable for many clinical chemistries. However, the use of the odd cycle with the corresponding freedom of movement of the reaction wheel 12 enables three component or trigger reagents to be utilized on the analyzer. Because such reagents can be injected into any one of the cuvettes on the reaction wheel 12 during an odd cycle, the reagent may be injected into an otherwise out-of-sequence cuvette before sample introduction or may be injected as a trigger component after sample introduction. Examples of chemistries requiring injection of the third component before sample introduction include creatinine kinase on the Astra ® System from Beckman Instruments, Inc., and examples of chemistries requiring a trigger component injection after sample introduction include EMIT ® chemistries from Syva.

The cuvettes in both the even and odd groups may run one or two reagent component chemistries as well as three component or triggered reagent chemistries. In such an instance, a third or trigger reagent can be injected into an even cuvette during the odd cycle immediately following the injection of the one or two initial reagents. However, odd cuvettes in which three component or triggered reagent chemistries are run would need to wait for a second cycle, that is, the next odd cycle, after initial reagent injection until the third or trigger reagent is injected. As an alternative, only the even group may run third or trigger reagent chemistries with the odd group restricted to one or two reagent chemistries, thus eliminating the potential two cycle wait otherwise possible with cuvettes in the odd group. It is to be understood that the trigger component may be a second or third reagent added to a cuvette in accordance with the timing requirements of the particular test.

Figure 3:
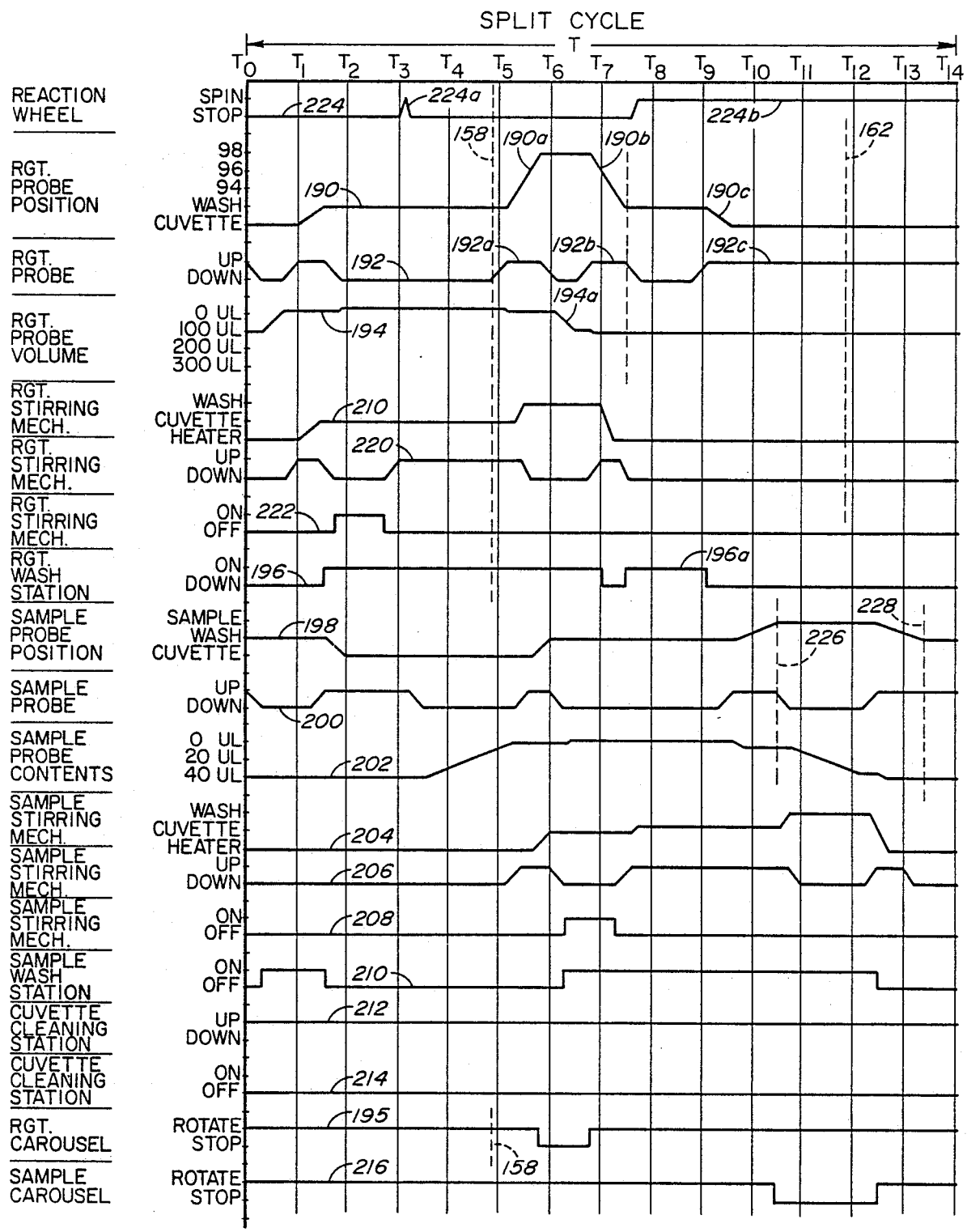
FIG. 3 is a timing diagram of actions occurring on the working surface of FIG. 1 during a second cycle timing of the operating method of the present invention.

Turning now to a more detailed description of the timing and logic of the method of the present invention, FIGS. 2 and 3 represent timing diagrams for normal and split cycle timing. Briefly, normal and split cycle timing each include the aspiration and injection of sample volumes from the sample carousel onto the reaction wheel. The normal timing as illustrated in FIG. 2 is performed for each even cycle and each even cuvette on the reaction wheel 12. The normal cycle is also used for odd cycles and odd cuvettes if only one or two component reagents need to be delivered during the cycle. If, however, the next odd cycle is to service a cuvette which requires a third reagent component or trigger reagent component, reagent handling is transferred at a decision time 158 to the split timing as illustrated in FIG. 3. At the end of the remaining actions in the normal timing, the next odd cycle is performed beginning with the split timing. The third or trigger component reagent is injected into the out-of-sequence cuvette located at the reagent injection location 130. With the injection completed, the reaction wheel 12 rotates to position the next-in-sequence cuvette at the sample injection location 121 and the remainder of the split timing is performed for the sample injection and stirring. However, once the third or trigger reagent is injected, reagent handling is transferred at the decision time 158 to the timing shown in the normal timing of FIG. 2 to load the reagent probe with the reagents required for the next even cycle.

Continuing now with a detailed description of normal and split timing as shown in FIGS. 2 and 3, both normal and split timing spans a period T beginning at T0 and ending at T14. The period T represents the period of a cycle. Times T14 and T0 overlap to provide cycle-to-cycle continuity. In the embodiment disclosed herein, each of the time periods between T0-T14 may be one second. However, the timing for the various elements of the analyzer as shown by the curves may be adjusted in accordance with the particular performance capabilities of the elements with corresponding adjustments in the overall time period T.

The timing and logic diagram of FIG. 2 represents the operation of the analyzer during normal timing. It is assumed that the normal timing is initially being performed during an even cycle. The reaction wheel 12 is stopped or stationary from time T0 to a time slightly before T8 (curve 150). While the reaction wheel 12 is stopped (150a), reagent and sample injection occur and cuvette washing is performed. The reaction wheel 12 then spins (150b) until just before time T14 and the polychromatic device 38 operates as described above to collect data points for the reaction locations.

The operation of the reagent transfer mechanism 22 is illustrated with reference to reagent probe horizontal position curve 152, reagent probe vertical position curve 154, reagent probe volume curve 156 and reagent wash station on-off curve 157. The reagent probe 126 is initially positioned above the cuvette at the reagent injection location 130. Beginning at time T0, the probe 126 is displaced vertically down into the cuvette (154a). The contents of the probe 126 (obtained as described hereinbelow) are injected into the cuvette (156a). Before time T3, the reagent probe is lifted out of the cuvette, rotated along the arc 128 to the wash station 134 and lowered into the wash station 134 (152a, 154b) where the reagent probe 126 exterior is washed (157a). The probe 126 interior may be washed by flowing wash fluid through the probe 126 and into the wash station 134. Small volume changes illustrated at 156b, 156h and 156i represent air bubbles expelled from or inducted into the probe 126.

At a time slightly before T5, the control circuitry of the apparatus determines whether the next cycle, that is, an odd cycle, requires a third or trigger reagent injection. If so, the operation of the reagent transfer and stirring mechanisms 22 and 24, the reaction wheel 12 and the reagent carousel 16 is transferred from the normal timing of FIG. 2 to the split timing of FIG. 3 at a common decision time 158. Otherwise, reagent transfer and stirring mechanisms 22 and 24, reaction wheel 12 and reagent carousel 16 operation continues with the normal cycle of FIG. 2. Assuming that the normal cycle is to continue, the reagent delivery probe 126 moves to the opening 96 and is inserted into the reagent cartridge 72 (154c, 152b) and withdraws a predetermined volume of reagent from the first compartment 74 (156c).

If a second reagent is to be drawn into the probe 126 for delivery during the next cycle, the operation continues by moving the probe to the wash station 134 (154d, 152c, 157b) for probe tip washing. The reagent probe 126 is moved to the opening 97, down into the second compartment 76 of the cartridge 72 and additional reagent is withdrawn into the probe (152d, 154e, 156d).

With the second reagent withdrawn into the probe 126, the probe is again moved to the wash station (152e, 154f) where the wash station is activated (157c) to wash the tip of the probe 126. The probe 126 is then moved to its home position above the reagent injection location 130 (152f and 154g) just prior to time T14.

If a second reagent is not to be withdrawn into the probe 126, the probe tip is washed and probe movements are suspended at decision time 160 through times T10-T11 and resumed at a time 162 just before the probe 126 is moved to its home position.

The operation of the reagent stirring mechanism 24 is illustrated with reference to horizontal position curve 164, vertical position curve 166 and on-off curve 168. The stirring mechanism 24 begins normal timing with the stirring member 124 at a home position within the heating station 138 (164a, 166a). After reagent injection as described above, the stirring member 124 is rotated into stirring position above the reagent injection location 130, lowered into the cuvette, and the stirring member 124 is rotated (164b, 166b and 168a). With stirring completed, the stirring member 124 is withdrawn, moved slightly to the side of the reagent injection location 130 (164c, 166c), moved to the wash station 134 for washing after probe 126 washing is completed (164d, 166d and 157a) and then returned to its home position within the heating station 138 (164e, 166e) for the remainder of the normal timing.

The operation of the sample transfer mechanism 18 is illustrated with respect to sample probe horizontal position curve 170, sample probe vertical position curve 172, sample probe volume curve 174, and sample wash station operation curve 176. The sample probe exterior is first washed at the wash station 132 (170a, 172a, 176a). The probe interior may be washed by flowing wash fluid through the probe 100 into the wash station 132. After the reagent probe 126 has delivered reagent to the cuvette positioned at the reagent injection location 130 as described above, the sample delivery probe 100 moves to the sample injection location 121 and injects its contents (obtained as described hereinbelow) into the cuvette at such location (170b, 172b and 174a). The sample probe 100 is again washed (170c, 172c, 176b), moves to the appropriate sample pickup position above the sample carousel 60, is lowered into the sample cup and withdraws a predetermined sample volume (170d, 172d and 174b). The sample probe 100 next moves to its home position above the wash station 132 (170e, 172e) where it remains until the end of the normal cycle at time T14. Small volume changes 174c, 174d and 174e represent air bubbles either expelled from or inducted into the sample probe 100.

The positioning and timing of the sample stirring mechanism 20 is illustrated with reference to a sample stirring mechanism horizontal position curve 178, a sample stirring mechanism vertical position curve 180 and a sample stirring mechanism on-off curve 182. The stirring mechanism 20 begins normal timing with the stirring member 124 at a home position within the heating station 136 (178a, 180a). Once the sample probe has injected sample as just described, the sample stirring mechanism 20 is moved into operating position inside the cuvette disposed at the sample injection location 121 (178b, 180b) and the stirring member 124 is rotated (182a) to stir the contents of the cuvette. The stirring mechanism is slightly to the side of the sample injection location 121 (178c, 180c), moved to the wash station 132 where the stirring member 124 is washed after sample probe 100 washing is completed (178d, 180d, 176b). With washing completed, the stirring mechanism is moved to its home position (178e, 180e).

The cuvette washing station 42 is operated in accordance with curves 183, 184. During even cycles, the station 42 is operated (184a). However, during odd cycles, the station 42 is not operated (183a, 184b), thus not interfering with the rotation of the reaction wheel 12 between reagent and sample injection.

Curves 186 and 188 illustrate times during the normal timing that the reagent carousel 16 and sample carousel 60, respectively, may rotate without interference from the reagent or sample probes 126, 100. It is to be recognized that the reagent and sample carousels 16 and 60 need not necessarily rotate during the indicated time periods but are free to do so as may be necessary to position various reagent cartridges 72 and sample sectors 58 under the reagent and sample probe arcs 128, 120.

As discussed above, reagent transfer mechanism 22 operation transfers to the split cycle timing of FIG. 3 at the decision time 158 if the next odd cycle requires the injection of a third or trigger component. In FIG. 3, the movement of the reagent transfer mechanism 22 is illustrated with respect to horizontal probe position curve 190, probe vertical position curve 192, probe volume curve 194, and reagent wash station on-off curve 6. Beginning at the decision time 158, the reagent probe 126 moves to the opening 98 and down into the third chamber 78 of the cartridge 72 (190a, 192a). Reagent from the third compartment is drawn into the probe (194a) and the probe 126 moves to the wash station 134 (190b, 192b). The wash station 134 operates (196a) to wash the probe 126. The probe 126 moves to its home position above the reagent injection location 130 (190c, 192c).

Reaction wheel 12 operation during the portion of the split timing described above is illustrated at curve 224. After the common decision time 158, the reaction wheel 12 rotates (224b) and the polychromatic device 38 gathers data for the cuvettes 34 carried by the reaction wheel 12. The reaction wheel 12 comes to rest with a cuvette positioned at the reagent injection location 130 that is to receive the third or trigger reagent component. Such cuvette is not the next cuvette in sequence that would otherwise receive reagent during the odd cycle but is located elsewhere on the reaction wheel 12.

With the beginning of the next odd cycle, the split timing as illustrated in FIG. 3 commences at time T0. The sample transfer mechanism 18, sample stirring mechanism 20, and sample carousel 60 operate generally as previously described for the normal timing and is illustrated with reference to timing curves 198-216. Because an odd cycle is being performed, the cuvette cleaning station 42 does not operate (curve 212).

Beginning at time zero through the decision time 158, the reagent transfer mechanism 20 and the reagent stirring mechanism 24 (curves 190-194 and 218-222) operate to inject the third or trigger component into the cuvette at the reagent injection location 130 and to stir the contents in a fashion similar to the injection and stirring described with reference to FIG. 2. At the decision time 158, the operation of reagent transfer and stirring mechanisms 22 and 24, the reaction wheel 12 and the reagent carousel 16 revert to the normal timing as shown in FIG. 2 beginning at the decision time 158. This transfer enables the reagent probe 126 to be loaded with one or two reagents as described above for injection during the next (even) cycle.

As seen in FIG. 3 with respect to reaction wheel rotation curve 224, once the reagent has been injected, the reaction wheel 12 is free to rotate (224a) so as to position the next-in-sequence cuvette in the sample injection location 121 for sample injection as illustrated with respect to curves 198–202 and stirring as illustrated with respect to curves 204–208.

As can be appreciated by those skilled in the art, not all of the reaction locations 30 may be active, that is, controlled so as to receive reagent and sample, at one time if maximum analyzer throughput is not required. Thus, if the next cuvette in sequence is inactive, the reagent transfer mechanism and associated elements suspend operation at the common decision time 158 and resume at the time 158 on the next cycle. Similarly, if a next cuvette for sample injection is inactive, the sample transfer mechanism 18 suspends operation at a time 226 and resumes operation at the time 226 on the next cycle.

It will also be apparent that if a third or trigger component is injected into an out-of-sequence cuvette during an odd cycle, reagents may not be injected into the cuvette that would otherwise be sequentially positioned under the reagent injection location 130 during the odd cycle. Thus, such locations are deemed inactive, that is, do not receive reagents or sample.

It will also be appreciated that while a specific embodiment of the present invention has been disclosed, the invention is not to be limited thereby but is to be afforded the full scope of the appended claims.

We claim:

1. A method of operating an analyzer wherein the analyzer includes a plurality of reaction locations for conducting analyses of samples, comprising the steps of:
   dividing the reaction locations into a first group and a second group;
   performing predetermined operations for the first and second groups during corresponding first and second processing cycles;
   performing an operation that is required for selected reaction locations in both the first and second groups during only the first processing cycle, the required operation being washing the selected reaction locations in adjacent reaction locations; and
   the predetermined operations including injecting samples and reagents into the reaction locations.

2. A method as in claim 1 wherein reagent injection occurs in sequential reaction locations during the first processing cycle and reagent injection may occur during the second processing cycle in either sequential reaction locations or out-of-sequence reaction locations.

3. A method as in claim 2 wherein sample injection is adapted to occur in sequential reaction locations.

4. A method as in claim 1 wherein the washing operation is performed during sample and reagent injection.

5. A method as claimed in claim 1 wherein the required operation is performed simultaneously in both the first and second groups of reaction locations.

6. A method as claimed in claim 1 wherein each cycle includes a degree of rotation.

7. A method of operating an analyzer, wherein the analyzer includes a reaction wheel adapted to receive a plurality of reaction locations and such reaction locations are divided into first and second groups of locations positioned at first and second positions on the reaction wheel, comprising the steps of:
   injecting reagent from a first group of reagents into a first reaction location included in the first group;
   injecting sample into a second reaction location included in the first group;
   washing at least two reaction locations on the reaction wheel, the two reaction locations including locations in the first and second groups;
   performing an analysis cycle for at least some of the locations on the reaction wheel;
   injecting reagent from the first group of reagents into a reaction location included in the second group of locations and sequentially related to the first reaction location, or injecting reagent from a second group of reagents into a reaction location not sequentially related to the first reaction location;
   injecting sample into a reaction location included in the second group and sequentially related to the second reaction location; and
   performing an analysis cycle for at least some of the locations on the reaction wheel.

8. A method as in claim 7 wherein reaction locations in which samples and reagents are injected to perform analyses are active locations and all reaction locations in the first group are adapted to be active locations and selected ones of the locations in the second group are active locations, and the second step of injecting reagent includes injecting reagent into the sequentially related reaction location in the second group if such reaction location is active.

9. A method as in claim 8 wherein the second step of injecting reagent includes rotating the reaction wheel to an active location disposed in the first group and injecting reagent into such location if the sequentially related reaction location in the second group is inactive.

10. A method as claimed in claim 7 wherein washing the reaction locations of the first and second groups is effected simultaneously.

11. A method of operating an analyzer wherein the analyzer includes a plurality of serially arranged reaction locations, the method comprising the steps of:
   performing successive processing cycles and, during at least a part of each processing cycle, positioning the reaction locations at a plurality of operation stations, wherein the positioning includes sequentially advancing the reaction locations by a predetermined increment with each successive processing cycle;
   at a first one of the operation stations, performing a first operation during selected ones of the processing cycles on at least a predetermined number of reaction locations that advance through the first operation station during the cycle that the first operation station operates and the processing cycle or cycles during which the first operation station does not operate;
   at a second one of the operation stations, performing a second operation on the sequentially positioned reaction location during the processing cycles that the first operation station operates, and performing the second operation either on the sequentially positioned reaction locations or on an out-of-sequence reaction location during the processing cycles that the first operation station does not operate; and
   at a third one of the operation stations, performing a third operation on the sequentially positioned reaction locations during each processing cycle.

12. A method as in claim 11 wherein the selected ones of the processing cycles comprise every other processing cycle.

13. A method as in claim 11 wherein selected ones of the reaction locations are inactive and the steps of performing the second and third operations include omitting the second and third operations for inactive reaction locations.

14. A method as in claim 11 wherein the first operation is washing the predetermined number of reaction locations.

15. A method as in claim 14 wherein the second operation includes injecting one or more reagents and the third operation includes injecting samples.

16. A method as in claim 15 wherein the second operation precedes in time the third operation during each processing cycle and wherein the step of positioning the reaction locations includes repositioning the reaction locations during the processing cycles for which the first operation station does not operate from out-of-sequence reagent injection to sequential sample injection.

17. A method as in the claim 15 wherein the washing operation is performed concurrently with at least one of the second and third operations.

18. A method as claimed in claim 15 wherein one of such reagents is a trigger reagent.

19. A method as claimed in claim 11 wherein the first operation is performed simultaneously on a predetermined number of reaction locations.

20. A method as claimed in claim 11 wherein each processing cycle includes a degree of rotation.

* * * * *

UNITED STATES PATENT AND TRADEMARK OFFICE
CERTIFICATE OF CORRECTION

PATENT NO. : 4,908,320
DATED : March 13, 1990
INVENTOR(S) : Zakowski, et al.

It is certified that error appears in the above-identified patent and that said Letters Patent is hereby corrected as shown below:

Col. 4, line 16 reads "74, 46, 78" should read --74, 76, 78--.

Col. 10, line 28 reads "on-off curve 6" should read --on-off curve 196--.

Signed and Sealed this

Twenty-second Day of March, 1994

Attest:

BRUCE LEHMAN

*Attesting Officer*  *Commissioner of Patents and Trademarks*